United States Patent
Iancea et al.

(10) Patent No.: US 6,190,360 B1
(45) Date of Patent: Feb. 20, 2001

(54) STENT DELIVERY HANDLE

(75) Inventors: Octavian Iancea, Fremont; Farhad Khosravi, San Mateo, both of CA (US)

(73) Assignee: Endotex Interventional System, Cupertino, CA (US)

(*) Notice: Under 35 U.S.C. 154(b), the term of this patent shall be extended for 0 days.

(21) Appl. No.: 09/289,052

(22) Filed: Apr. 9, 1999

(51) Int. Cl.[7] .................................................. A61M 5/178
(52) U.S. Cl. ............................ 604/164.09; 604/164.12
(58) Field of Search ............................ 604/158, 165.01, 604/167.02, 264, 168, 154, 160, 164.04, 164.09, 164.1, 164.11, 164.12, 165.02

(56) References Cited

U.S. PATENT DOCUMENTS

| | | | |
|---|---|---|---|
| 5,209,741 | * | 5/1993 | Spaeth ............................ 604/164 X |
| 5,290,310 | | 3/1994 | Makower et al. . |
| 5,312,351 | * | 5/1994 | Gerrone ............................ 604/167 X |
| 5,391,172 | | 2/1995 | Williams et al. . |
| 5,409,478 | | 4/1995 | Gerry et al. . |
| 5,433,723 | | 7/1995 | Lindenberg et al. . |
| 5,601,568 | | 2/1997 | Chevillon et al. . |
| 5,697,948 | | 12/1997 | Marin et al. . |
| 5,704,914 | * | 1/1998 | Stocking et al. .................. 604/167 X |
| 5,707,376 | | 1/1998 | Kavteladze et al. . |
| 5,759,186 | | 6/1998 | Bachmann et al. . |
| 5,868,755 | | 2/1999 | Kanner et al. . |
| 5,906,595 | * | 5/1999 | Powell et al. ......................... 604/167 |
| 5,906,619 | | 5/1999 | Olson et al. . |
| 6,053,934 | | 4/2000 | Andrews et al. . |

OTHER PUBLICATIONS

PCT Publication No. WO 99/49808, Pasul Gilson, et al., "A Delivery Catheter", Oct. 7, 1999.

* cited by examiner

Primary Examiner—Anhtuan T. Nguyen
(74) Attorney, Agent, or Firm—Lyon & Lyon LLP

(57) ABSTRACT

A handle device for a catheter-sheath assembly includes a handle member having proximal and distal ends, and a control member including a tubular portion coupled to a control portion, the control portion slidably coupled to the handle member. A cooperating rail and wheel are provided on the handle member and the control portion for directing the control portion axially with respect to the handle member upon rotation of the wheel. A tubular sheath extends distally from the tubular portion, and a catheter or bumper is secured to the handle member that extends through the tubular portion into the sheath. The control portion is directable between distal and proximal positions to direct the tubular portion proximally and consequently retract the sheath with respect to the catheter or bumper to deploy a stent or other element from within the sheath.

38 Claims, 3 Drawing Sheets

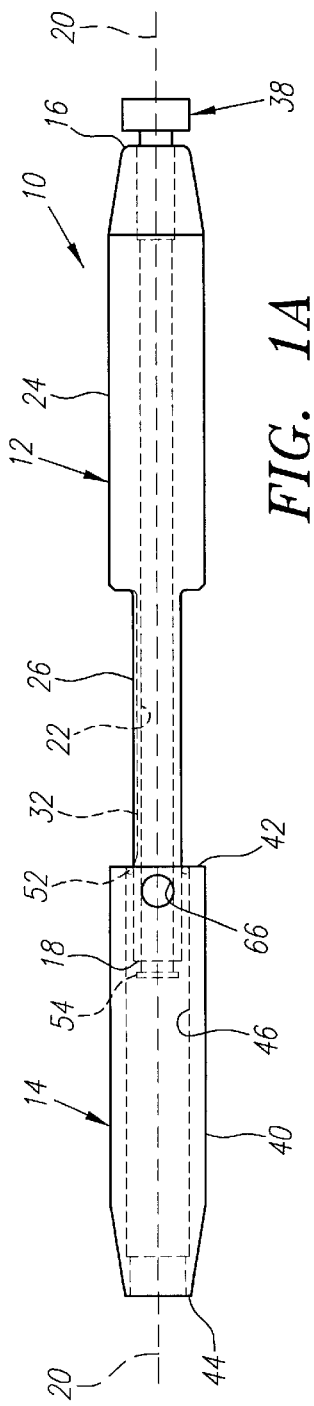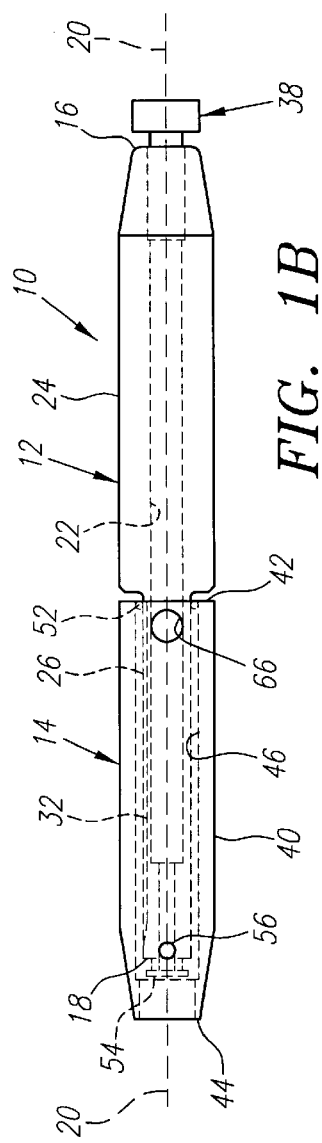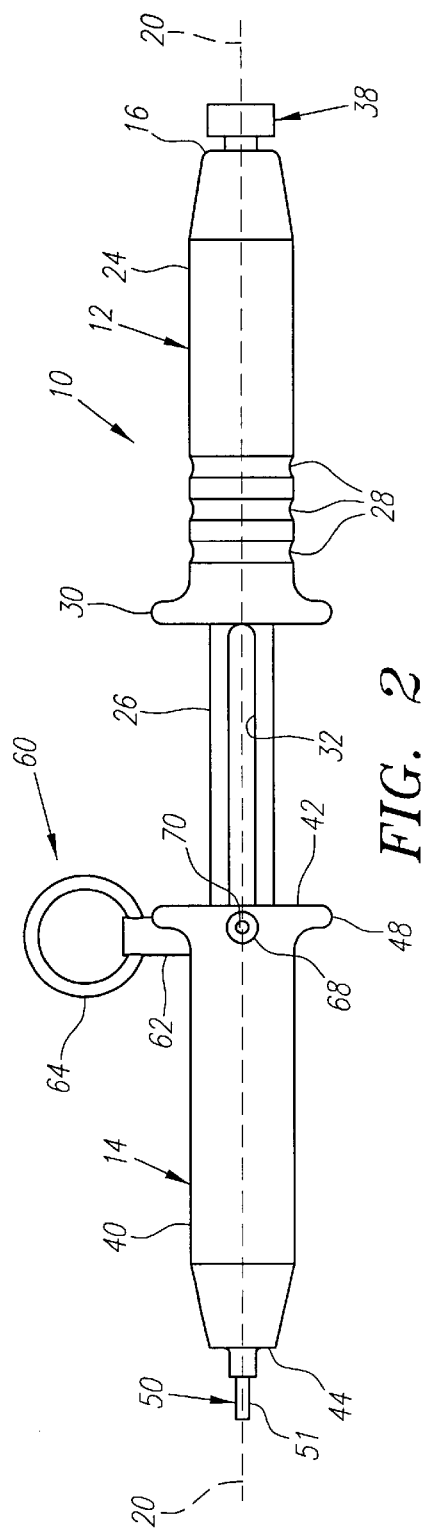

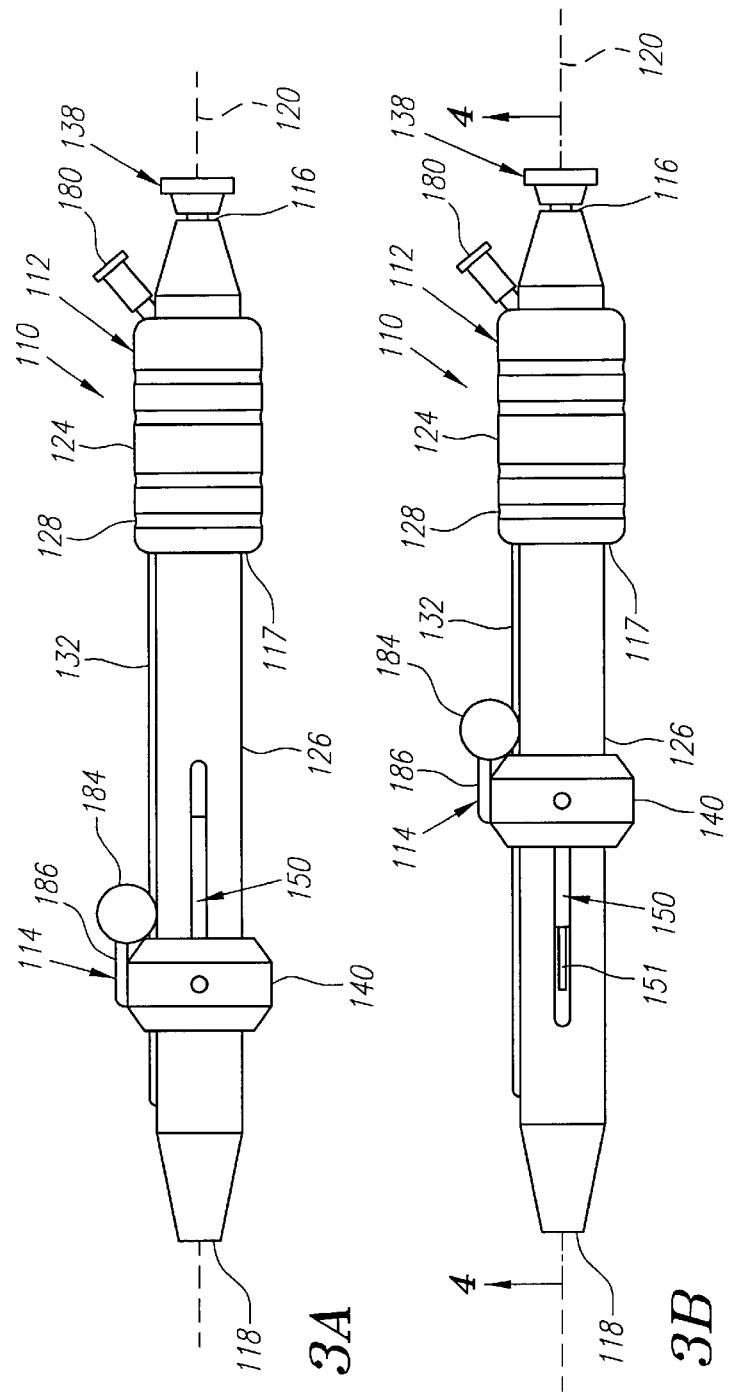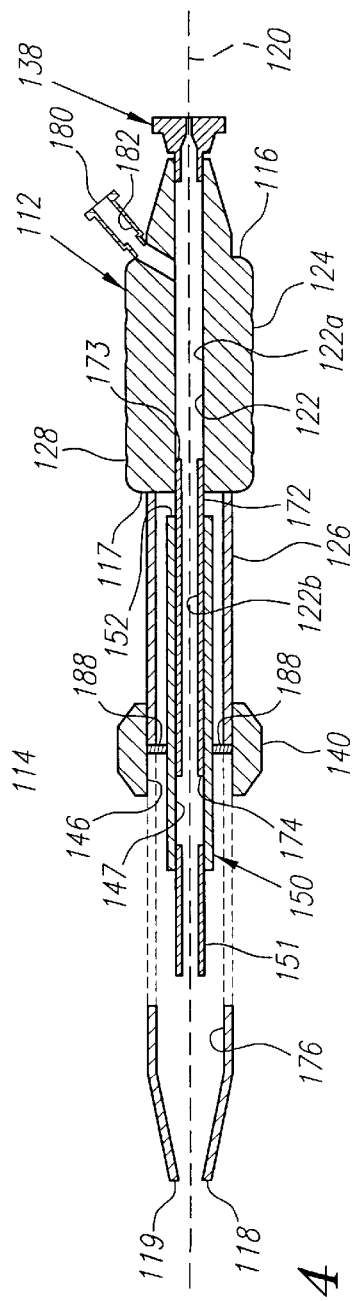
FIG. 3A    FIG. 3B    FIG. 4

STENT DELIVERY HANDLE

FIELD OF THE INVENTION

The present invention relates generally to catheter-based systems for treating a remote location within a patient, and more particularly to handles for stent delivery systems, electrophysiology devices and the like, which include a catheter and a retractable sheath thereon.

BACKGROUND

Devices having a retractable sheath associated with a catheter are used to treat a variety of conditions using endoluminal methods instead of open surgical procedures. For example, angioplasty and stent implantation procedures are often used to treat atherosclerotic disease or other occlusive conditions in blood vessels, such as the coronary and carotid arteries. During angioplasty, a catheter having an uninflated balloon on its distal end is percutaneously introduced into a patient's vasculature and advanced to a target treatment location, such as a stenosis within a blood vessel. Once the balloon is properly placed across the stenosis, the balloon is inflated to enlarge the lumen at the location. The balloon is then deflated, the inflation/deflation procedure may be repeated, and then the catheter is withdrawn from the patient's body.

Often in conjunction with angioplasty, a stent or other tubular prosthesis may be implanted within a stenosis to scaffold the location and prevent it from contracting or otherwise becoming obstructed again. The stent is generally placed upon a catheter in a contracted condition, possibly over a balloon, the catheter advanced to the target stenosis until the stent is placed across the location, and then the stent is deployed and substantially anchored at the location. The stent may be biased to expand to an enlarged condition and/or may be expanded with the aid of a balloon, as with plastically deformable stents, until the stent substantially engages the wall of the vessel. Once the stent is implanted, the delivery catheter is withdrawn from the patient.

Similarly for ablation procedures and the like, a catheter including an array of electrodes, for example, on an expandable basket assembly, may be provided. The device may be introduced into a body lumen, for example through the patient's vasculature into the heart, to treat conditions, such as heart arrhythmia.

With any of these systems, a sheath may be provided over the distal end of the catheter to protect the components on the distal end, such as a balloon, a stent or an array of electrodes. The sheath may be advanced distally over the proximal end of the catheter until it covers the distal end and its components, or the distal end of the catheter may be introduced into the sheath, and advanced until it is proximate the distal end of the sheath. Once the distal end of the catheter is properly positioned at a desired location within a body lumen, the sheath may be retracted to expose the distal end of the catheter. After treatment, the sheath may be advanced back over the distal end of the catheter, and the entire device withdrawn from the patient.

To cause the sheath to retract, the proximal end of the sheath outside the patient may simply be pulled while holding the catheter in a fixed position. This, however, may not provide very precise control of the retraction of the sheath. To provide improved control, handle devices have been proposed which include a wheel and screw mechanism. A wheel extending around the circumference of the handle is coupled to a screw mechanism engaging the sheath and the catheter. As the wheel is rotated about the longitudinal axis of the handle, the screw mechanism directs the sheath axially with respect to the catheter.

With such devices, however, it may be difficult to remember which direction, i.e., clockwise or counterclockwise, is appropriate either to retract or advance the sheath with respect to the catheter. This may be particularly important when immediate action is necessary because of a complication during a procedure. In addition, these screw-type devices may be complicated, including many parts which may be difficult to assemble and/or expensive to make.

Accordingly, there is a need for more intuitive, more simple and/or less expensive devices for controlling catheter-sheath systems.

SUMMARY OF THE INVENTION

The present invention is directed to a handle device for an endoluminal apparatus that includes an outer tubular member and an elongate inner member slidably received in the outer tubular member. The handle device may include as few as two pieces, namely a handle member and a control member slidably associated with one another. The handle member preferably has proximal and distal ends and proximal and distal portions defining a longitudinal axis therebetween, and having a lumen extending axially between the proximal and distal ends. In a preferred form, the proximal portion includes gripping elements, and the distal portion has a relatively narrow cylindrical shape.

The handle member may include a locking mechanism thereon having an open position for allowing an elongate member, such as a catheter, to be inserted into the lumen in the handle member, and a closed position for fixing the axial position of the elongate member with respect to the handle member. In a preferred form, the locking mechanism also provides a hemostatic seal on the proximal portion of the handle member.

The control member is slidably coupled to the handle member and includes a tubular portion aligned concentrically with the lumen in the handle member and a control portion slidably received on the distal portion of the handle member. The control portion is slidable axially with respect to the handle member between distal and proximal positions.

Preferably, the control portion of the control member has a tubular shape defining a passage into which the distal portion of the handle member is slidably received. A proximal seal may be provided on the control portion of the control member for slidably engaging the distal portion of the handle member to facilitate sealing of the passage. In addition, a distal seal may be provided on the distal portion of the handle member for slidably engaging the control portion of the control member to further seal the passage. One of the proximal and distal seals may include an air vent for releasing air from within the passage when the control portion is directed proximally.

A locking mechanism may be provided for substantially securing the control portion in one of its proximal and distal positions. In a preferred form, the locking mechanism is a removable pin extending into both the control portion and the handle member, which may, for example, substantially secure the control portion in its distal portion to prevent premature retraction of a sheath coupled to the handle device.

In addition, the handle device also preferably includes a rail extending axially along the distal portion of the handle member, and a guide member on the control portion engaging the rail for preventing rotation of the control portion relative to the handle member about the longitudinal axis. In a first preferred embodiment, the rail may be an axial groove formed in the distal portion of the handle member, and the guide member may be an extension element, such as a tab or screw, extending from the control portion into the groove. In another preferred embodiment, the rail may be a raised rail member extending axially along the distal portion of the handle member, which may be attached to or integrally formed as part of the distal portion. The guide member may include a thumb wheel rotatably mounted to the control portion of the control member, the wheel engaging the rail member for directing the control portion axially upon rotation of the wheel.

In a preferred embodiment, the tubular portion of the control member may be disposed in the lumen of the handle member, and the tubular portion may be coupled to the control portion such that the tubular portion is directed axially within the lumen when the control portion is directed axially. Preferably, the tubular portion of the control member is coupled to the control portion by one or more hubs extending therebetween. The hubs preferably travel in an axial slot in the distal portion of the handle member, thereby limiting the relative axial movement of the control portion and the handle member. More preferably, the tubular portion of the control member travels in an enlarged region of the lumen of the handle member. A tubular extension portion may extend from the proximal portion of the handle member into the enlarged region of the lumen. The tubular extension portion may slidably engage an interior of the tubular portion of the control member, preferably providing a fluid-tight seal therebetween.

The handle device may be incorporated into an apparatus for treating a remote location within a body lumen of a patient, such as a catheter-sheath assembly. A tubular outer member, such as a retractable sheath, may be attached to and may extend distally from the tubular portion of the control member. An elongate inner member, such as a catheter device, may be directed through the lumen in the handle member and through the tubular portion of the control member into the outer member. The inner member may be substantially secured axially with respect to the handle member by the locking mechanism.

Preferably, the outer member has a distal end, and the inner member has a distal end disposed proximate the distal end of the outer member when fully received in the handle device. Thus, the outer member may subsequently be directable between distal and proximal positions when the control portion is directed between its distal and proximal positions, for covering and uncovering, respectively, the distal end of the inner member beyond the distal end of the outer member. The inner member preferably has a treatment element on its distal end, such as an expandable prosthesis, the prosthesis being deployable when the distal end of the inner member is uncovered from the outer member. Alternatively, or in addition, the treatment element may include an expandable member, such as an angioplasty balloon. In further alternatives, the treatment element may include an array of electrodes, which may be mounted directly on the inner member, or may be provided on an expandable frame or basket assembly.

During use of the catheter-stent assembly, the distal end of the sheath may be introduced into a patient, and advanced to a target treatment location. Once in place, the control member may be directed proximally, thereby retracting the sheath and exposing the distal end of the catheter, and preferably, the treatment element thereon. The control member may be directly manipulated by pulling the control portion proximally to retract the sheath, or by placing a thumb on the thumb wheel and directing the thumb proximally along the upper circumference of the wheel. Thus, the manipulation of the control member corresponds substantially to the consequential movement of the sheath, thereby providing an intuitive means for controlling the retraction of the sheath.

Other objects and features of the present invention will become apparent from consideration of the following description taken in conjunction with the accompanying drawings.

BRIEF DESCRIPTION OF THE DRAWINGS

FIGS. 1A and 1B are side views of a first preferred embodiment of a handle device, in advanced and retracted positions, respectively, in accordance with the present invention.

FIG. 2 is a side view of the handle device of FIG. 1A, including a locking mechanism for securing the handle device in its advanced position.

FIGS. 3A and 3B are side views of a second preferred embodiment of a handle device, in advanced and retracted positions, respectively.

FIG. 4 is a cross-sectional view of the handle device of FIG. 3B, taken along line 4—4.

DETAILED DESCRIPTION OF THE PREFERRED EMBODIMENTS

Figure 5:
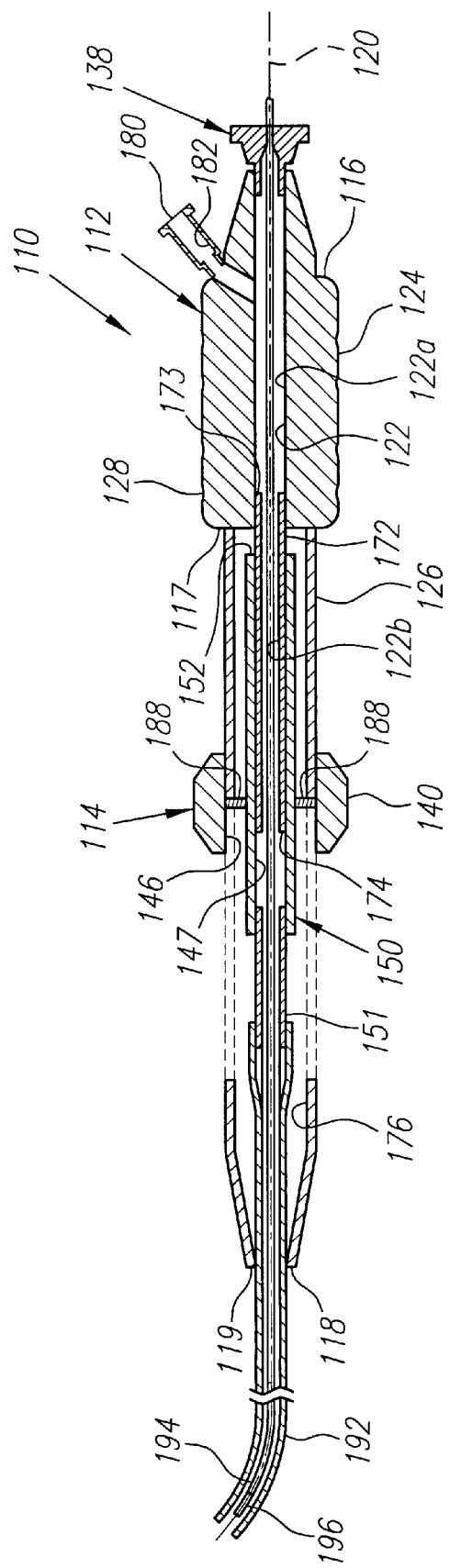
FIG. 5 is another cross-sectional view of the handle device of FIG. 3B, taken along line 4—4, including a sheath and catheter attached thereto.

Turning now to the drawings, FIGS. 1A, 1B and 2 show a handle device 10 in accordance with the present invention that may include as few as two parts, namely a proximal or handle member 12 and a distal or control member 14 slidably associated therewith. The handle and control members 12, 14 may be made from similar materials, for example, molded from plastic or machined from metal, such as stainless steel. The handle and control members 12, 14 may provide a slidable seal therebetween, or one or more seals may be provided between them, as described further below.

The handle member 12 is a generally elongate member having proximal and distal ends 16, 18 defining a longitudinal axis 20 therebetween, and a lumen 22 extending axially between the proximal and distal ends 16, 18. Preferably, the handle member 12 includes an enlarged proximal portion 24, and a relatively narrow distal portion 26. The proximal portion 24 may include gripping elements, such as a plurality of annular grooves 28 or a raised annular ridge or finger grip 30 (see FIG. 2) to facilitate holding the handle device 10. The distal portion 26 preferably has a substantially uniform cylindrical cross-section including an elongate groove 32 therein, which extends substantially parallel to the longitudinal axis 20.

A hemostatic valve assembly 38 may be provided on the proximal end 16 of the handle member 12. The valve assembly 38 provides a sealable opening in communication with the lumen 22 for allowing an elongate member, such as a stent delivery catheter (not shown), to be introduced into the lumen 22 from the proximal end 16 of the handle device 10. The valve assembly 38 may also provide a locking mechanism, i.e., may be adjustable between an open position for allowing an elongate member to be easily inserted into the lumen 22, and a closed position for fixing the axial position of the elongate member with respect to the handle member 12.

The control member 14 includes a tubular-shaped gripping or control portion 40 having proximal and distal ends 42, 44 and defining a passage 46 extending axially therethrough. The control portion 40 may include gripping elements, similar to the proximal portion 24 of the handle member 12, such as a raised annular ridge or finger grip 48 (see FIG. 2). The distal portion 26 of the handle member 12 is received within the passage 46 such that the control portion 40 may slide axially with respect to the handle member 12 between a distal position (FIG. 1A) and a proximal position (FIG. 1B). Preferably, the passage 46 and the distal portion 26 of the handle member 12 have similar cross-sections, such as a cylindrical shape, that facilitates the axial movement of the control portion 40 with respect to the handle member 12 with minimal lateral movement.

In addition, a guide member may be provided on the control member 14 for preventing rotational movement of the control member 14 about the longitudinal axis 10 with respect to the handle member 12. For example, a set screw 68 may be threaded into a mating hole 70 in the control portion 40 adjacent its proximal end 42. When fully seated, the set screw 68 may extend into the passage 46 within the control portion 40 such that when the hole 70 is properly aligned with the groove 32 in the distal portion 26 of the handle member 12, the set screw 68 slidably engages the groove 32.

Alternatively, the guide member may be a tab (not shown) molded directly to the control portion 40. In a further alternative, instead of a groove 32, a raised rail (not shown) may be provided, e.g., integrally molded to the distal portion 26 of the handle member 12, and a corresponding groove (not shown) may be provided in the control portion 40 that extends axially from its proximal end 42 into the passage 46. A cooperating rail and guide member may prevent twisting of a sheath (not shown) attached to the control member 14 relative to the handle member 12, and consequently, relative to a catheter (not shown) introduced through the lumen 22 in the handle member 12.

The control member 14 preferably also includes a tubular distal portion (not shown in FIGS. 1A and 1B) aligned concentrically with the lumen 22 in the handle member 12. The tubular distal portion may be integrally formed as part of the control portion 40, or alternatively, may be a separate component removably or permanently attached thereto. For example, as shown in FIG. 2, a nipple 50 may be attached to the distal end 44 of the control member 14 for receiving the proximal end of a sheath (not shown) thereon. The nipple 50 may have a threaded proximal end (not shown) adapted to engage similar threads in the distal end 44 and/or the nipple 50 may be substantially secured to the distal end 44 by a friction fit, an adhesive and the like. The distal end 51 of the nipple 50 preferably has an outside diameter corresponding substantially to the inside diameter of the sheath (not shown) to be received thereon, which may be retained simply by friction or may be bonded thereto, for example, by an adhesive.

In addition, seals may be provided for sealing the passage 46 within the control member 14 and/or the lumen 22 of the handle member 12, for example, to prevent blood or other fluid from leaking out of, or air from leaking into, the handle device 10 during use. A proximal seal 52 may be provided on the proximal end 42 of the control member 14 for sealing the slidable connection between the control member 14 and the distal portion 26 of the handle member. A piston seal 54 may be provided on the distal end 18 of the handle member 12 for engaging the inner surface of the control portion 40 to further seal the passage 46. Preferably, an air vent 56 is provided in the piston seal 54 to allow air to escape from the passage 46 when the control member 14 is directed axially.

The handle device 10 also preferably includes a locking mechanism for substantially securing the control member 14 in a predetermined position, e.g., one of its proximal and distal positions. In a preferred form, a removable pin 60 is provided which engages both the control member 14 and the handle member 12 for substantially securing the control member 14 in its distal position. The pin 60 may include an elongate cylindrical pin member 62 to which a finger ring 64 is attached.

An opening 66, having a cross-section similar to the pin member 62, may extend through the control member 14, and a similarly shaped recess (not shown) may be provided in the distal portion 26 of the handle member 12 that may be aligned with the opening 66 when the control portion 40 is directed to its distal position. The pin member 62 may then be inserted through the opening 62 and into the recess, thereby substantially securing the control portion 40 axially with respect to the handle member 12.

A tamperproof seal (not shown) may be provided to demonstrate that the handle device 10 has not been previously activated, i.e., that the control portion 40 has never been moved from its distal position. For example, a tearable or breakable band (not shown), which may have an identifying label thereon to identify the device, may be wrapped around the control portion 40 and through the finger ring 64. At any time, for example, when it is desired to retract a sheath coupled to the control member 14, the band may be broken, allowing the pin 60 to be removed from the recess and opening 66, and thereby permitting the control portion 40 to be directed axially.

Turning to FIGS. 3A, 3B and 4, a second preferred embodiment of a handle device 110 is shown. Similar to the previous embodiment, the handle device 110 includes a handle member 112 having a gripping proximal portion 124 and relatively narrow distal portion 126, and a control member 114 having a control portion 140 coupled to a tubular portion 150. The handle member 112 has proximal and distal ends 116, 118 defining a longitudinal axis 120 therebetween. A lumen 122 extends axially from the proximal end 116 through a tubular extension 172 to a distal tip 174 of the tubular extension 172. The handle member 112 also includes an elongate passage 176 that extends axially within the distal portion 126 from the distal end 118 to the distal edge 117 of the proximal portion 124, and generally surrounds the tubular extension 172.

The proximal portion 124, distal portion 126 and tubular extension 172 may be integrally formed as one piece, or alternatively, may be formed as two or three separate pieces which are attached together, for example, by bonding with an adhesive and the like. For example, if the handle member 112 is provided as these three separate parts, a proximal end 173 of the tubular extension 172 may be partially inserted into the lumen 122a within the proximal portion 124 and attached thereto. The distal portion 126 may then be directed over the tubular extension and attached to the distal edge 117 of the proximal portion 124.

The proximal end 166 of the handle member 112 may have a lockable seal member 138, similar to the previous embodiment, for introducing a catheter (not shown) into the lumen 122. In addition, a flush port 180 may be attached to the handle member 112, preferably extending generally laterally from the proximal portion 124 adjacent the proximal end 116. The flush port 180 may communicate through a flush lumen 182 with the lumen 122, thereby facilitating the introduction of fluid to flush the lumen 122, as will be appreciated by those skilled in the art. The proximal portion 124 may also include gripping elements, such as annular grooves 128 to facilitate holding of the handle device 110.

A rail member 132 may be provided on the distal portion 126 of the handle member, which, in a preferred form, is an elongate cylindrical rod, for example, machined from stainless steel. The rail member 132 may be attached to the distal edge 117 of the proximal portion 124 and/or may be attached along its length to the distal portion 126. Alternatively, the rail member 132 may be integrally molded as part of the distal portion 126 (not shown).

The control portion 140 of the control member 114 generally has an annular shape defining a passage 146 therethrough through which the distal portion 126 of the handle member 112 may be slidably received. The passage 146 preferably includes an elongate axial groove (not shown) having a cross-section similar to the rail member 132 for facilitating slidable engagement therebetween to prevent rotation of the control portion 140 about the longitudinal axis 120 with respect to the handle member 112.

A thumb wheel 184 is rotatably mounted to the control portion 140 to facilitate manipulation of the control portion 140, preferably by an arm 186, such that the axis of rotation of the thumb wheel 184 is substantially perpendicular to the longitudinal axis 120. The thumb wheel 184 preferably includes a pair of circular wheels, connected by a hub (not shown), that straddle the rail member 132. The arm 186 preferably terminates in a "C" shaped socket (not shown) for receiving the hub of the thumb wheel therein, thereby allowing the hub to rotate freely and substantially engage the rail member 132.

When the thumb wheel 184 is rotated, for example, by placing a thumb on the upper circumference of the thumb wheel 184 and directed the thumb axially, the hub frictionally engages the rail member 132 to move the control portion 140 axially as the hub rolls along the rail member 132. For example, when the user places their thumb on the thumb wheel 184 and directs their thumb proximally, the control portion 140 will follow their motion and be directed proximally. Alternatively, the wheels on the thumb wheel 184 may engage the surface of the distal portion 126 to move the control portion 140. A circumferential surface of the wheels may be roughened to increase the frictional contact between the wheels and the surface of the distal portion 126. and/or between the wheels and thumb of the user.

As best seen in FIG. 4, the tubular portion 150 of the control member 114 is axially disposed within the passage 176 within the distal portion 126 of the handle member 112. The tubular portion 150 has a lumen 147 therein which extends from its proximal end 152 to a distal or nipple end 151. The nipple 151 may be integrally molded to the tubular portion 150 or may be a separate piece attached thereto.

The tubular portion 150 is coupled to the control portion 140, for example, by a pair of hubs 188 that extend therebetween substantially perpendicular to the longitudinal axis 120. The hubs 188 preferably extend through elongate axial slots 190 in the distal portion 126 of the handle member, thereby limiting the relative axial movement of the control member 114 with respect to the handle member 112, i.e., thereby defining a distal position (FIG. 3A) and a proximal position (FIG. 3B) for the control member 114. The hubs 188 may be integrally formed as part of one of the control portion 140 and the tubular portion 150 or may be separate rod-like or tubular sections that are mounted between the control portion 140 and the tubular portion 150, for example, by threaded hubs, screws, adhesives and the like (not shown). In a preferred form, the control portion 140 includes openings (not shown) through which the hubs 188 may be received and secured, for example, with set screws.

During assembly, the tubular portion 150 may be introduced through an opening 119 in the distal end 118 of the handle member 112, or the tubular portion 150 may be directed into the passage 176 prior to attachment of the distal portion 126 to the proximal portion 124 of the handle member. The tubular portion 150 may be advanced over the tubular extension 172 of the handle member 112, preferably providing a slidable seal therebetween. Alternatively, one or more seals (not shown) may be provided within the lumen 147 of the tubular portion 150, similar to the seals described above. The hubs 188 may be aligned with the slots 190, the control portion 140 may be directed over the distal portion 126 until the control portion 140 is properly aligned with the hubs 188. The hubs 188 may then be attached to the control portion 140, for example, using set screws and/or adhesives, as will be appreciated by those skilled in the art.

Turning to FIG. 5, during use, a sheath 192 may be directed into the opening 119 in the distal end 118 of the handle member 112 and attached to the nipple end 151 of the tubular portion 150 of the control member 114. For example, the nipple end 151 may have an outer diameter corresponding to the inner diameter of the sheath 192 to provide a frictional fit therebetween and/or the sheath 192 may be bonded to the nipple end 151. Thus, when the control portion 140 is directed axially, the 192 sheath is advanced or retracted with respect to the distal end 118.

A catheter or other rail 194 may be provided having a distal end with a treatment element 196 thereon, such as an angioplasty balloon, a stent or other prosthesis, and/or an array of electrodes (not shown). The hemostatic valve 138 on the handle member 112 may be opened, and the distal end of the catheter 194 may be introduced through the hemostatic seal 138 into the lumen 122. The distal end of the catheter 194 may be advanced through the lumen 147 in the tubular portion 150 of the control member into the sheath lumen until the distal end is proximate a distal end of the sheath, 192 i.e., until the treatment element 196 is positioned adjacent the distal end of the sheath 192. The hemostatic valve 138 may then be closed, substantially sealing the lumen 122, and substantially securing the catheter 194 to the handle member 112. Alternatively, the catheter 194 may be introduced into the distal end of the sheath 192 and directed proximally until its proximal end exits the hemostatic valve 138.

The catheter-sheath assembly may then be introduced into a patient, for example, percutaneously into a peripheral artery or other blood vessel, and advanced to a target treatment location, such as a stenosis or other lesion (not shown). The treatment element may be positioned with respect to the treatment location, e.g., to position a stent across a stenotic region, for example, using radiopaque markers associated with the distal end of the catheter-sheath assembly.

The control member 114 may then be used to retract the sheath and expose the treatment element, for example, to deploy a stent on the catheter. The control portion 140 may be directed proximally by engaging the upper circumference of the thumb wheel 184 with the user's thumb, and directing their thumb proximally. This action directs the tubular portion 150 proximally, thereby retracting the sheath proximally a corresponding distance, and exposing the distal end of the catheter and/or the treatment element associated therewith. Thus, manipulation of the sheath may be achieved using the handle device 110 in a very intuitive manner, without requiring the user to question which direction the control portion 140, and consequently the sheath coupled to the control member 114, will move when they direct their thumb axially over the thumb wheel 184. The thumb wheel 184 also may facilitate more precise control of the sheath retraction.

The previous embodiment of the handle device 10 shown in FIG. 2 may be used in a similar manner, except that the control portion 40 may be directly manipulated, for example, by grabbing the finger grip 48 and pulling the control portion 14 proximally to retract a sheath (not shown) coupled to the tubular distal portion 50 of the control member 14. The travel of the control portion 40 is also inherently intuitive because of the direct relationship between manipulation of the handle device 10 and the resulting movement of the sheath. The handle device 10 provides a direct feedback loop to the user that allows them to tactilely sense the distal end of the sheath, e.g., to "feel" the ease with which the stent is retracting, which is an important when treating a patient remotely using endoluminal procedures.

In addition, it may be desirable to provide distance demarcations or notches at predetermined intermediate locations on the distal portion 26, 126 of the handle devices 10, 110 described herein. For example, if multiple treatment elements are placed on the distal end of a catheter, the sheath may be retracted partially, i.e., to one or more intermediate positions, to uncover sequentially the treatment elements for use.

In a further alternative, a sheath-bumper assembly (not shown) may be attached to the handle devices 10, 100. A sheath may be attached to the distal portion 50, 150 of the control member 14, 114, and a bumper member may be inserted through the hemostatic seal 38, 138 and axially secured with respect to the handle member 12, 112. Preferably, the sheath and bumper member have a predetermined relative length such that when the control member 14, 114 is in its distal position, the distal end of the sheath extends a predetermined distance beyond the distal end of the bumper member, thereby defining a recess within the distal end of the sheath for receiving an expandable prosthesis therein. When the sheath is retracted by directing the control member 12, 112 to its proximal position, the bumper member may hold the prosthesis in position, thereby deploying the prosthesis from the recess into a target location within the patient, as will be appreciated by those skilled in the art.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for treating a remote location within a body lumen of a patient, comprising:

a handle member having proximal and distal ends and proximal and distal portions defining a longitudinal axis therebetween, and a lumen therein extending between the proximal and distal ends;

a control member comprising a tubular portion aligned with the lumen of the handle member and a control portion slidably coupled to received on the distal portion of the handle member, the control portion being directable axially with respect to the handle member between distal and proximal positions;

a tubular outer member extending distally from the tubular portion of the control member;

an elongate inner member extending through the lumen in the handle member and through the tubular portion of the control member into the outer member, the inner member being substantially secured axially with respect to the handle member;

a rail extending axially along the distal portion of the handle member; and a guide member on the control member engaging the rail for preventing rotation of the control member relative to the handle member about the longitudinal axis.

2. The apparatus of claim 1, wherein the outer member has a distal end, and the inner member has a distal end disposed proximate the distal end of the outer member, and wherein the outer member is directable between distal and proximal positions when the control portion is directed between its distal and proximal positions, for covering and uncovering, respectively, the distal end of the inner member.

3. The apparatus of claim 2, wherein the inner and outer members have a predetermined relative length such that when the outer member is in its distal position, the distal end of the outer member extends a predetermined distance beyond the distal end of the inner member, thereby defining a recess for receiving an expandable prosthesis therein.

4. The apparatus of claim 2, wherein the inner member has a treatment element on its distal end.

5. The apparatus of claim 4, wherein the treatment element comprises an expandable prosthesis, the prosthesis being deployable when the distal end of the inner member is uncovered from the outer member.

6. The apparatus of claim 4, wherein the treatment element comprises an expandable member.

7. The apparatus of claim 1, wherein the handle member comprises a locking mechanism thereon having an open position for allowing the inner member to be inserted into the lumen in the handle member, and a closed position for substantially securing the relative axial position of the inner member and the handle member.

8. The apparatus of claim 7, wherein the locking mechanism comprises a hemostatic seal on the proximal portion of the handle member.

9. The apparatus of claim 1, further comprising a locking mechanism for substantially securing the control member in one of its proximal and distal positions.

10. The apparatus of claim 9, wherein the locking mechanism comprises a removable pin extending into both the control member and the handle member.

11. The apparatus of claim 1, wherein the control portion comprises a finger grip.

12. The apparatus of claim 1, wherein the control portion of the control member has a tubular shape defining a passage into which the distal portion of the handle member is slidably received.

13. The apparatus of claim 1, wherein the rail comprises an axial groove formed in the distal portion of the handle member, and the guide member comprises an extension element extending from the control member into the groove.

14. The apparatus of claim 1, wherein the rail comprises a rail member extending axially along the distal portion of the handle member.

15. The apparatus of claim 14, wherein the guide member comprises a wheel rotatably mounted to the control portion of the control member, the wheel engaging the rail member for directing the control portion axially upon rotation of the wheel.

16. The apparatus of claim 1, wherein the tubular portion of the control member is disposed in the lumen of the handle member, the tubular portion being coupled to the gripping portion such that the tubular portion is directed axially within the lumen when the gripping portion is directed axially.

17. The apparatus of claim 16, wherein the tubular portion of the control member is coupled to the gripping portion by a hub extending therebetween, the hub traveling in an axial slot in the distal portion of the handle member, thereby limiting the relative axial movement of the control portion and the handle member.

18. The apparatus of claim 16, wherein the tubular portion of the control member travels in an enlarged region of the lumen of the handle member.

19. The apparatus of claim 18, further comprising a tubular extension portion extending distally from the proximal portion of the handle member into the enlarged region of the lumen, the tubular extension portion slidably engaging an interior of the tubular portion of the control member.

20. An apparatus for treating a remote location within a body lumen of a patient, comprising:
  a handle member having proximal and distal ends defining a longitudinal axis therebetween;
  a control member comprising a tubular portion and a control portion slidably coupled to the handle member, the control portion being directable axially with respect to the handle member between distal and proximal positions;
  a tubular outer member attached to a distal end of the tubular portion of the control member and extending distally therefrom; the tubular outer member being directed proximally as the control portion is directed between its distal and proximal positions;
  an elongate inner member secured to the handle member and extending through the tubular portion of the control member into the outer member; and
  a treatment element disposed in a lumen of the tubular outer member proximate its distal end, the elongate inner member being configured for holding the treatment element in position when the tubular outer member is being directed proximally, thereby deploying the treatment element from within the lumen of the tubular outer member.

21. The apparatus of claim 20, wherein the outer member has a distal end, and the inner member has a distal end disposed proximate the distal end of the outer member, and wherein the outer member is directable between distal and proximal positions when the control portion is directed between its distal and proximal positions, for covering and uncovering, respectively, the distal end of the inner member.

22. The apparatus of claim 21, wherein the inner member has the treatment element on its distal end.

23. The apparatus of claim 22, wherein the treatment element comprises an expandable prosthesis.

24. The apparatus of claim 22, wherein the treatment element comprises an expandable member.

25. The apparatus of claim 21, wherein the inner and outer members have a predetermined relative length such that when the outer member is in its distal position, the distal end of the outer member extends a predetermined distance beyond the distal end of the inner member, thereby defining a recess for receiving the treatment element therein.

26. The apparatus of claim 25, wherein the treatment element comprises an expandable prosthesis.

27. The apparatus of claim 26, wherein the inner member comprises a bumper for preventing proximal movement of the expandable prosthesis received in the recess when the outer member is directed proximally.

28. The apparatus of claim 20, further comprising a seal for providing a fluid-tight seal between the control member and the lumen.

29. An apparatus for treating a remote location within a body lumen of a patient, comprising:
  a handle member having proximal and distal ends defining a longitudinal axis therebetween, and including a lumen extending parallel to the longitudinal axis;
  a control member comprising a tubular portion and a control portion slidably received on the handle member, the control portion being directable axially with respect to the handle member between distal and proximal positions;
  a tubular outer member extending distally from the tubular portion of the control member, the tubular outer member being directed proximally as the control portion is directed between its distal and proximal positions;
  an elongate inner member extending through the lumen in the handle member and through the tubular portion of the control member into the outer member; and
  a cooperating rail and wheel on the handle and the control portion of the control member, the wheel engaging the rail for directing the control portion axially upon rotation of the wheel.

30. An apparatus for treating a remote location within a body lumen of a patient, comprising:
  a handle member having proximal and distal ends defining a longitudinal axis therebetween;
  a control member comprising a tubular portion coupled to a control portion, the control portion being slidably coupled to the handle member such that the control portion is directable axially with respect to the handle member to direct the tubular portion axially;
  a tubular outer member extending distally from the tubular portion of the control member;
  an elongate inner member secured to the handle member and extending through the tubular portion of the control member into the outer member; and
  a cooperating rail and wheel on the handle member and the control portion of the control member, the wheel engaging the rail for directing the control portion axially upon rotation of the wheel, thereby directing the tubular outer member axially with respect to the elongate inner member.

31. The apparatus of claim 30, further comprising a treatment element disposed within a lumen of the tubular outer member proximate its distal end.

32. The apparatus of claim 31, wherein the treatment element comprises a stent.

33. The apparatus of claim 32, wherein the elongate inner member comprises a bumper member having a distal end proximate the stent, whereby when the control portion is directed proximally, the outer tubular member retracts while the bumper holds the stent in position to deploy the stent from the outer tubular member.

34. The apparatus of claim 30, wherein the tubular outer member has a distal end, and the elongate inner member has a distal end disposed proximate the distal end of the tubular outer member, and wherein the tubular outer member is directable between distal and proximal positions when the control portion is directed between its distal and proximal positions, for covering and uncovering, respectively, the distal end of the elongate inner member.

35. The apparatus of claim 30, wherein the elongate inner member and the tubular outer member have a predetermined relative length such that when the tubular outer member is in its distal position, the distal end of the tubular outer member extends a predetermined distance beyond the distal end of the elongate inner member, thereby defining a recess for receiving an expandable prosthesis therein.

36. The apparatus of claim 35, further comprising an expandable prosthesis received in the recess.

37. The apparatus of claim 35, wherein the inner member comprises a bumper member for preventing proximal movement of an expandable prosthesis received in the recess when the outer member is directed proximally.

38. The apparatus of claim 30, further comprising a seal for providing a fluid-tight seal between the control member and the lumen.

* * * * *

UNITED STATES PATENT AND TRADEMARK OFFICE
CERTIFICATE OF CORRECTION

PATENT NO. : 6,190,360 B1
DATED : February 20, 2001
INVENTOR(S) : Iancea et al.

It is certified that error appears in the above-identified patent and that said Letters Patent is hereby corrected as shown below:

Column 7,
Lines 56 and 57, change "ther-ebetween" to -- there-between --.

Column 8,
Line 29, change "192 sheath" to -- sheath 192 --.
Line 42, change "sheath, 192" to -- sheath 192, --.

Signed and Sealed this

Twenty-third Day of April, 2002

Attest:

JAMES E. ROGAN
*Attesting Officer*  *Director of the United States Patent and Trademark Office*